(12) United States Patent
Newman et al.

(10) Patent No.: US 10,028,697 B2
(45) Date of Patent: *Jul. 24, 2018

(54) SYSTEM AND METHOD FOR MEASURING SKIN MOVEMENT AND STRAIN AND RELATED TECHNIQUES

(71) Applicant: Massachusetts Institute of Technology, Cambridge, MA (US)

(72) Inventors: Dava J. Newman, Cambridge, MA (US); Ashley M. Mateus, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 371 days.

This patent is subject to a terminal disclaimer.

(21) Appl. No.: 14/837,455

(22) Filed: Aug. 27, 2015

(65) Prior Publication Data

US 2016/0317079 A1 Nov. 3, 2016

Related U.S. Application Data

(63) Continuation of application No. 13/274,992, filed on Oct. 17, 2011.

(51) Int. Cl.
*A61B 5/00* (2006.01)
*A61B 5/11* (2006.01)

(52) U.S. Cl.
CPC .......... *A61B 5/442* (2013.01); *A61B 5/1121* (2013.01); *A61B 5/1127* (2013.01); *A61B 5/7225* (2013.01); *A61B 5/7278* (2013.01); *A61B 5/0064* (2013.01); *A61B 5/0077* (2013.01); *A61B 5/6828* (2013.01); *A61B 2562/0261* (2013.01)

(58) Field of Classification Search
CPC ...... A61B 5/442; A61B 5/0064; A61B 5/0077
See application file for complete search history.

(56) References Cited

U.S. PATENT DOCUMENTS

| | | |
|---|---|---|
| 4,000,524 A | 1/1977 | Rinehart |
| 4,654,896 A | 4/1987 | Rinehart |
| 4,969,106 A | 11/1990 | Vogel et al. |
| 5,056,530 A | 10/1991 | Butler et al. |

(Continued)

FOREIGN PATENT DOCUMENTS

| | | |
|---|---|---|
| WO | WO 93/22624 | 11/1993 |
| WO | WO 2009/100020 A4 | 8/2009 |

(Continued)

OTHER PUBLICATIONS

Ross et al., Recovery Force_1: U.S. Appl. No. 61/701,329, filed Sep. 14, 2012; 18 pages.

(Continued)

*Primary Examiner* — Sean Dougherty
(74) *Attorney, Agent, or Firm* — Daly, Crowley, Mofford & Durkee, LLP

(57) ABSTRACT

Described herein are systems and techniques for a motion capture system and a three-dimensional (3D) tracking system used to record body position and/or movements/motions and using the data to measure skin strain (a strain field) all along the body while a joint is in motion (dynamic) as well as in a fixed position (static). The data and technique can be used to quantify strains, calculate 3D contours, and derive patterns believed to reveal skin's properties during natural motions.

20 Claims, 9 Drawing Sheets

(56) References Cited

U.S. PATENT DOCUMENTS

| | | | |
|---|---|---|---|
| 5,167,038 | A | 12/1992 | Rinehart |
| 5,641,955 | A | 6/1997 | Bonniau et al. |
| 5,757,473 | A | 5/1998 | Kanduth et al. |
| 6,345,191 | B1 | 2/2002 | Hartmann et al. |
| 6,389,200 | B1 | 5/2002 | Foltzer |
| 6,809,462 | B2 | 10/2004 | Pelrine et al. |
| 7,281,275 | B2 | 10/2007 | Bitzer |
| 2003/0013994 | A1 | 1/2003 | Rubinstenn et al. |
| 2003/0065278 | A1 | 4/2003 | Rubinstenn et al. |
| 2005/0264561 | A1 | 12/2005 | Angst et al. |
| 2006/0056661 | A1 | 3/2006 | Einighammer et al. |
| 2007/0167879 | A1 | 7/2007 | Cochran |
| 2007/0186642 | A1 | 8/2007 | Sano et al. |
| 2008/0234607 | A1 | 9/2008 | Hunter-Jones et al. |
| 2009/0255531 | A1 | 10/2009 | Johnson et al. |
| 2009/0315989 | A1 | 12/2009 | Adelson |
| 2010/0000547 | A1 | 1/2010 | Johnson et al. |
| 2011/0288447 | A1 | 11/2011 | Cochran |
| 2011/0319791 | A1 | 12/2011 | Harry et al. |
| 2012/0238914 | A1 | 9/2012 | Goldfield et al. |
| 2013/0116601 | A1 | 5/2013 | Tomazic et al. |
| 2014/0081187 | A1 | 3/2014 | Wyatt et al. |
| 2014/0277739 | A1 | 9/2014 | Kornbluh et al. |
| 2014/0311187 | A1 | 10/2014 | Amarasiriwardena et al. |
| 2015/0073318 | A1 | 3/2015 | Holschuh et al. |
| 2015/0073319 | A1 | 3/2015 | Holschuh et al. |

FOREIGN PATENT DOCUMENTS

| | | |
|---|---|---|
| WO | WO 2011/109029 A1 | 9/2011 |
| WO | WO 2016/077150 A1 | 5/2016 |

OTHER PUBLICATIONS

Bethke, Kristen "The second skin approach: skin strain field analysis and mechanical counter pressure prototyping for advanced spacesuit design"; with Abstract and Chapters 3, 4 and 5, pp. 41-114 (78 pages), 2005; Retrieved from the Internet. <URL:http://dspace.mit.edu/bitstream/handle/1721.1/32443/61719483-MIT.pdf?sequence=2>.

PCT Search Report and Written Opinion of the ISA, PCT/US2015/053978 dated Jan. 6, 2016; 8 pages.

Bethke, et al.; "Bio-Suit Development: Viable Options for Mechanical Counter Pressure;" SAE Technical Paper Series; 34$^{th}$ International Conference on Environmental Systems (ICES); Jul. 19-22, 2004; 14 pages.

Newman, et al.; "Astronaut Bio-Suit System to Enable Planetary Exploration;" 55'th International Astronautical Congress; 2004; pp. 1-22.

Newman, et at; "Revolutionary Design for Astronaut Exploration—Beyond the Bio-Suit System;" vol. 880, Jan. 30, 2007; 12 pages.

Wolfrum, et al.; "An Automatic Procedure to Map the Skin Strain Field with Application to Advanced Locomotion Space Suit Design;" 5$^{th}$ World Congress of Biomechanics, Munich, Jul. 29-Aug. 4, 2006; 2 pages.

Iberall; "The Use of Lines of Nonextension to Improve Mobility in Full-Pressure Suits;" Technical Report—AMRL-TR-64-118; Wright-Patterson Air Force Base; Nov. 1964; 44 pages.

Iberall; "Use of Lines of Nonextension to Provide Mobility in Full-Pressure Suits;" an ASME Publication; American Society of Mechanical Engineers; Nov. 16-20, 1969; 17 pages.

Domingues, et al; "Skin Strain Field Analysis of the Human Ankle Joint;" 4$^{th}$ Congress Nacional De Biomecanica; Feb. 4-5, 2010; 6 pages.

Marreiros; "Skin Strain Field Analysis of the Human Ankle Joint;" Dissertation; Instituto Superior Tecninco; Faculdade De Medicina; Nov. 2010; 73 pages.

Non-Final Office Action dated Aug. 1, 2014 for U.S. Appl. No. 13/274,992; 20 pages.

Response filed on Dec. 1, 2014 to on Final Office Action dated Aug. 1, 2014; for U.S. Appl. No. 13/274,992; 21 pages.

Final Office Action dated Jan. 28, 2015, for U.S. Appl. No. 13/274,992; 11 pages.

Response filed on May 28, 2015 to Final Office Action dated Jan. 28, 2015; for U.S. Appl. No. 13/274,992; 7 pages.

Supplemental Response filed on Jun. 1, 2015 to Final Office Action dated Jan. 28, 2015; for U.S. Appl. No. 13/274,992; 12 pages.

Notice of Allowance dated Jun. 11, 2015, for U.S. Appl. No. 13/274,992; 9 pages.

Ambrosino, et al.; "Novel Magnetic Sensor Based on Fiber Bragg Grating and Magnetic Shape Memory Alloys;" 1$^{st}$ International Conference on Sensing Technology; Nov. 21-23, 2005; 6 pages.

Holschuh, et al.; "Morphing Compression Garments for Space Medicine and Extravehicular Activity Using Active Materials;" Aerospace Medicine and Human Performance; vol. 87; No. 2; Feb. 2016; 9 pages.

Holschuh, et al.; "Two-Spring Model for Active Compression Textiles with Integrated NiTi Coil Actuators;" IOP Publishing; Smart Materials and Structures; Feb. 6, 2015; 14 pages.

Park, et al.; "Exoskeletal Force-Sensing End-Effectors With Embedded Optical Fiber-Bragg-Grating Sensors;" IEEE Transactions on Robotics; vol. 25; No. 6; Dec. 2009; 13 pages.

Stirling, et al.; Applicability of Shape Memory Alloy Wire for an Active, Soft Orthotic; Journal of Materials Engineering and Performance; ASM International; Feb. 8, 2011; 5 pages.

Witt, et al.; "Medical Textiles with Embedded Fiber Optic Sensors for Monitoring of Respiratory Movement;" IEEE Sensors Journal; vol. 12; No. 1; Jan. 2012; 9 pages.

PCT International Preliminary Report on Patentability dated May 26, 2017 from International Application No. PCT/US2015/053978; 7 Pages.

SYSTEM AND METHOD FOR MEASURING SKIN MOVEMENT AND STRAIN AND RELATED TECHNIQUES

CROSS REFERENCE TO RELATED APPLICATIONS

This application is a continuation of, and claims the benefit under 35 U.S.C. § 120 of the filing date of, co-pending patent application Ser. No. 13/274,992, filed Oct. 17, 2011, all of which is incorporated by reference herein in its entireties.

STATEMENT REGARDING FEDERALLY SPONSORED RESEARCH

This invention was made with government support under Grant No. CNS0932015 awarded by the National Science Foundation and under Grant Nos. NAS5-03110 and NAS5-98051 awarded by NASA. The government has certain rights in this invention.

FIELD OF THE INVENTION

The concepts described herein relate to a system and technique for measuring and modeling skin movement and more particularly to a system and technique for quantifying skin movement and deriving strain fields, contours and three-dimensional patterns.

BACKGROUND OF THE INVENTION

As is known in the art, while there is extensive understanding of human skin properties based on active tensile testing, both in vitro and in vivo, there is little current knowledge of the strains experienced by skin during natural movements.

Understanding the skin's material properties and natural motion is important to help provide better understanding in a number of areas including: creating tissue engineering scaffolds that integrate smoothly with little scarring; understanding skin growth; aging; and changes due to diseases. Past work has been completed to ascertain material property data of isolated skin samples with in vitro tensile testing and by applying external loads (pulling, twisting, indenting, and suctioning) and measuring the resulting deformations in vivo. These experimental methods are limited because the skin behaves differently when removed from surrounding tissues in vitro and in vivo techniques do not take into account the skin's biaxial prestress. Because of the anisotropic behavior, it has been theorized that the skin contains lines of non-extension (LONEs), or contours of the skin that stay a constant length with minimal stretching capacity that only rotate during joint motion. As the body moves, particularly close to the joint, these LONEs do not always exist; in those cases the contours that are most important are those with the minimum extension or compression. Previous work, however, have only been able to qualitatively find non-extending lines.

SUMMARY OF THE INVENTION

The concepts, systems and techniques described herein result in a new understanding of the relationship between the structure of skin and the strains it experiences during natural joint movement. In particular, concepts, systems and techniques allow one to quantify strains, calculate three-dimensional (3D) contours, identify lines of non-extension (LONEs) and derive patterns that are believed to reveal skin's properties during natural motions. The system and techniques described herein may thus find application in a wide variety of areas including, but not limited to, design of tissue-engineering scaffolds, medical diagnosis for skin surgery, the design and development of soft exoskeletons, as well as commercial spacesuits and athletic garments.

In accordance with the concepts, systems and techniques described herein, a motion capture system (including a camera, video acquisition, processing and tracking markers) and a three-dimensional (3D) tracking system (e.g. a laser scanner) are used to record body movements/motions. By recording body movements/motions a new method is provided for measuring the skin's strain all along the body (a strain field) while a joint is in motion (dynamic) as well as in a fixed position (static). Thus, while prior art techniques were able to qualitatively find non-extending lines, having dynamic information during the entire motion, allows one to quantify strains, calculate 3D contours, and derive patterns that are believed to reveal skin's properties during natural motions.

From motion capture or laser scan position data, a lines of non-extension (LONEs) processor 522 calculates lines of non-extension by analyzing the changes in distance between each marker point and its closest neighbors from initial position to deformation, and calculating strain values. When a rectangular grid (such as that shown in FIGS. 3A, 3B is used), closest neighbors are considered to be the two markers adjacent in the same row and also the three markers in the rows above and below in the corresponding columns. In one embodiment, second order Lagrangian strains ε are calculated using the following equation (it should be noted that the second order equation is used because the strains are so large):

$$\varepsilon = \frac{l^2 - l_0^2}{2l_0^2} = \frac{\Delta l}{l_0} + \frac{(\Delta l)^2}{2l_0^2};$$

In which:
l is the new distance between two points
$l_0$ is the original length between two points, and
$\Delta l$ is the difference between the two.

The 3D strains surrounding each data point are projected onto a two-dimensional (2D) plane tangent to the body skin at each marker position. In one exemplary embodiment, this 2D plane is created by first averaging the normal vectors to the planes between each neighboring pair of strain vectors. This new "average" normal of (eight) 8 different planes defines the normal vector to the tangential plane created at the marker position. It should be appreciated that other techniques to compute the plane, may also be used. After being projected onto the tangential plane, the strains are then rotated in pairs onto the axes defined by the location of the marker directly above and then averaged together to give the longitudinal strain ($\varepsilon_y$), the circumferential strain ($\varepsilon_x$), and the shear strain ($\varepsilon_{xy}$).

This is followed by eigenvector analysis to determine the principle strains ($\varepsilon_I$ and $\varepsilon_{II}$). If the principle strains are of opposite signs, meaning there is both extension and compression, they are used to mathematically determine the angle of the lines of non-extension (φ) with the known equations:

$$\tan^2\phi = \frac{\varepsilon_I(2+\varepsilon_I)}{-\varepsilon_{II}(2+\varepsilon_{II})}$$

$$\tan^2\phi = \frac{(1-\varepsilon_I)^2(\varepsilon_I(2+\varepsilon_I))}{(1+\varepsilon_{II})^2(1-(1+\varepsilon_{II})^2)}$$

where the first equation is the angle between the primary eigenvector and the line of non-extension projected onto the initial position and the second equation is the same angle projected onto the deformed position. If the principle strains are of the same sign, meaning there is only local extension or local compression, then the minimum extension or minimum compression is recorded, respectively. These angles are projected onto the body surface (e.g., leg) and, during primarily stationary analysis only, they are connected to continuous lines (e.g. using basic spline functions). This method of finding tangent planes and creating strain tensors requires all eight (8) surrounding points. Other techniques may, of course, also be used.

With this particular methodology, body motion and skin movement are provided and skin-strain field analysis and patterning/contours are provided. In one embodiment, the motion capture system measures skin movement and strain around the knee during a squatting motion. It should, of course, be appreciated that the system and techniques described herein above are not limited to use with any particular body part (e.g. knee regions) or any particular motion (e.g. squatting), rather the system and techniques described herein may be used in any body region and for any body movement including body joint movements for dynamic motions (e.g., squatting, bending, walking, etc.).

In accordance with a further aspect of the concepts described herein, a new technique to analyze skin movement and strain for a static body as well as a body in motion (e.g. around the knee during a squatting motion) includes calculations of lines of non-extension, minimum and maximum skin movement, compression and tension.

In accordance with a further aspect of the concepts, systems and techniques described herein, a method for manufacturing a garment (e.g. an athletic garment, a spacesuit, etc. . . . ) comprises using a material formed into a shape by at least considering lines of non-extension of the body part over which the garment will be disposed wherein the lines of non-extension of the body part are determined, at least in part, from position data of body skin of the body part wherein the position data is generated from a plurality of position data points obtained at one or more locations defined by one or more corresponding markers disposed on the body skin wherein the position data is computed using an initial position and a deformed position and computing lines of non-extension from the position data measure at least at the initial position and a deformed position.

Thus, in accordance with a further aspect of the concepts, systems and techniques described herein, a method for design of tissue-engineering scaffolds comprises forming tissue-engineered scaffolds into a shape by at least considering lines of non-extension of the body part over which the tissue-engineered scaffolds will be disposed wherein the lines of non-extension of the body part are determined, at least in part, from position data of body skin of the body part wherein the position data is generated from a plurality of position data points obtained at one or more locations defined by one or more corresponding markers disposed on the body skin wherein the position data is computed using an initial position and a deformed position and computing lines of non-extension from the position data measure at least at the initial position and a deformed position.

Thus, in accordance with a further aspect of the concepts, systems and techniques described herein, a method for soft exoskeletons comprises forming a soft exoskeleton into a shape by at least considering lines of non-extension of the body part over which the tissue-engineered scaffolds will be disposed wherein the lines of non-extension of the body part are determined, at least in part, from position data of body skin of the body part wherein the position data is generated from a plurality of position data points obtained at one or more locations defined by one or more corresponding markers disposed on the body skin wherein the position data is computed using an initial position and a deformed position and computing lines of non-extension from the position data measure at least at the initial position and a deformed position.

BRIEF DESCRIPTION OF THE DRAWINGS

The foregoing features of the concepts, systems, circuits and techniques described herein may be more fully understood from the following description of the drawings in which:

FIG. 3A is the anterior of the leg and FIG. 3B is the posterior of the right leg;

DETAILED DESCRIPTION OF THE PREFERRED EMBODIMENTS

Figure 1A:
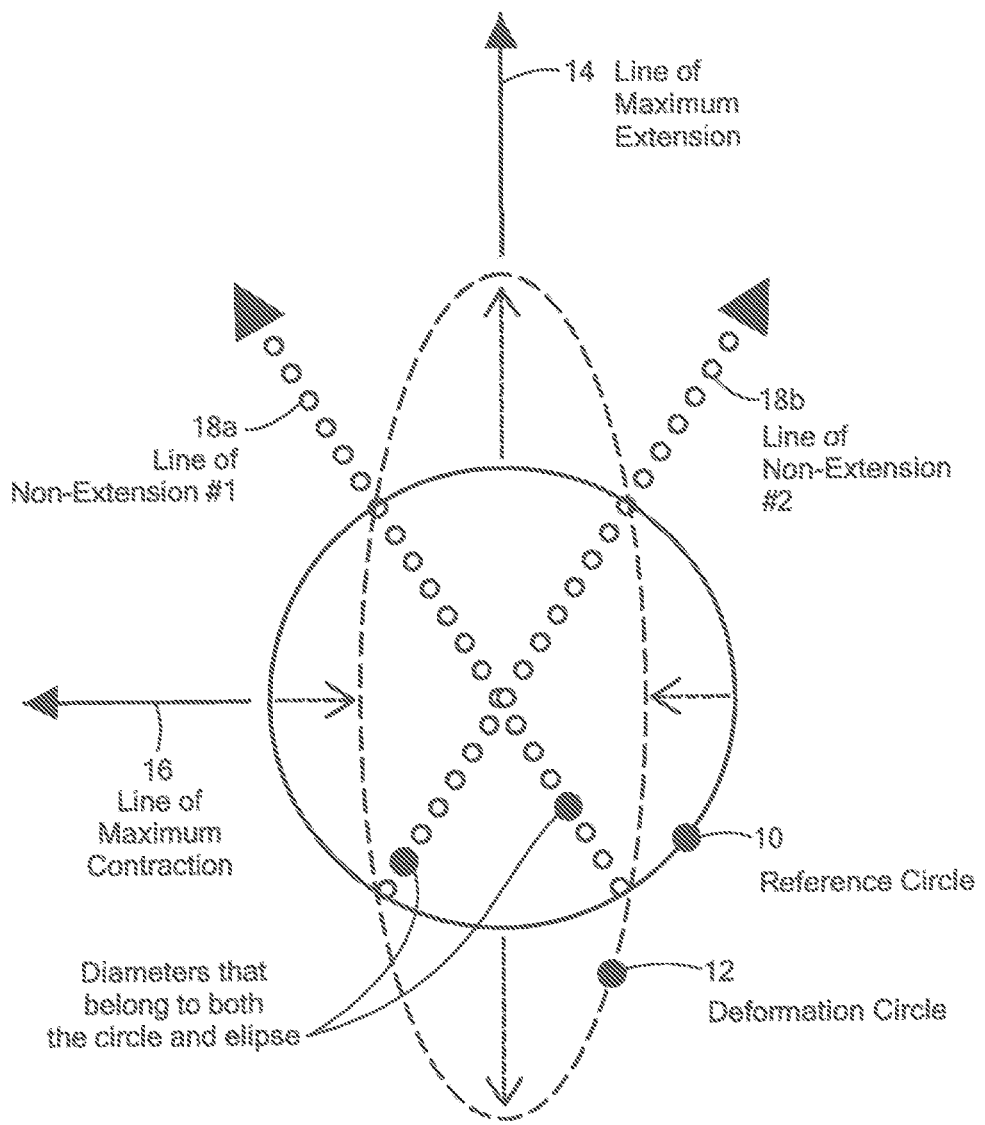
FIG. 1A is a graphical representation of lines of non-extension.

Referring now to FIG. 1A, a graphical representation of lines of non-extension includes a reference circle 10, a deformation circle 12, a line of maximum extension 14, a line of maximum contraction 16, and two lines of nonextension portions 18a, 18b of which illustrate diameters that belong to both the circle and the ellipse.

Figure 1D:
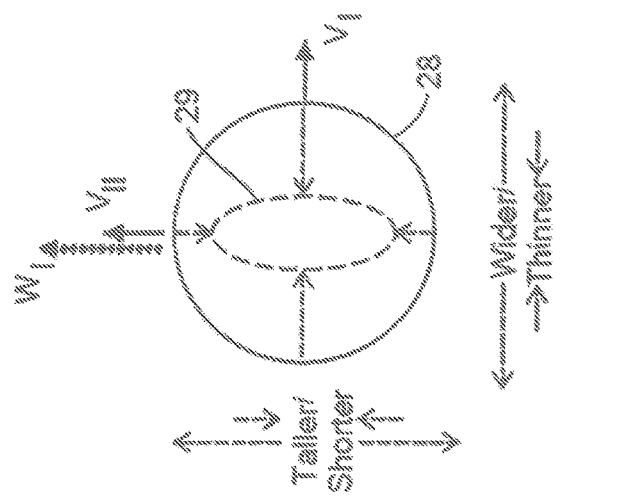
FIGS. 1B-1D illustrate three (3) cases of a deformation ellipse. The circle outlined in completed (i.e. solid) lines represents to initial position and the circle with dotted lines represents the deformed position. Case 1 (FIG. 1B): LONES exist. Case 2 (FIG. 1C)—complete extension: the important direction is the line of minimum extension. Case 3 (FIG. 1D)—complete compression: the important direction is the line of minimum compression.
Figure 1C:
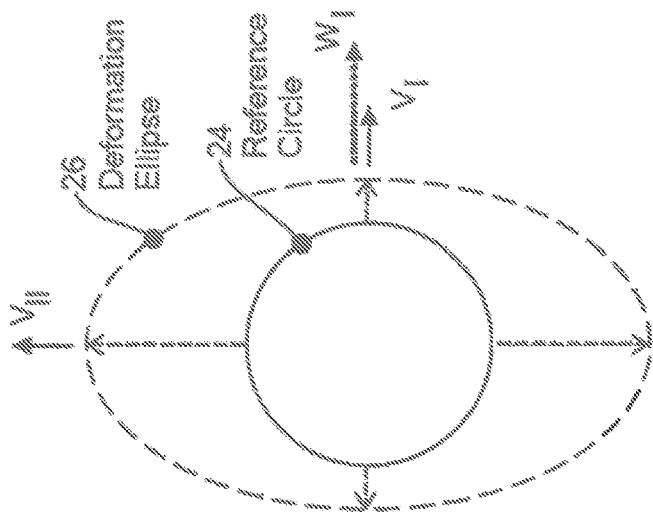
Figure 1B:
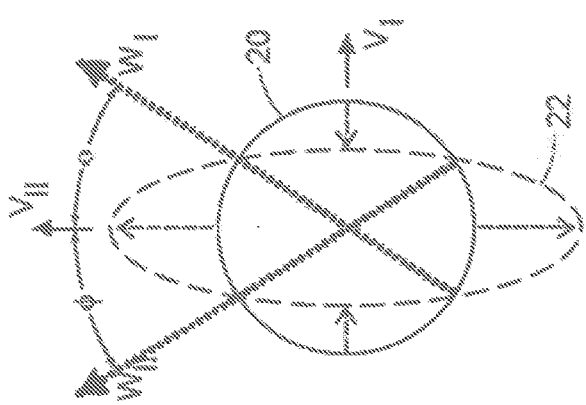

Referring now to FIGS. 1B-1D, three (3) cases of a deformation ellipse are shown. The circle outlined in completed (i.e. solid) lines 20 represents an initial position and the circle with dashed lines 22 represents a deformed position. As visible in FIG. 1B, (i.e. Case 1) lines of non-extension (LONES) exist.

Referring now to FIG. 1C, as with FIG. 1B, the circle outlined in completed (i.e. solid) lines 24 represents an initial position and the circle with dashed lines 26 represents a deformed position. As visible in FIG. 1C (i.e. Case 2—complete extension) the important direction is the line of minimum extension.

Referring now to FIG. 1D, as with FIGS. 1B and 1C, the circle outlined in completed (i.e. sold) lines 28 represents an initial position and the circle with dashed lines 29 represents a deformed position. As visible in FIG. 1D (Case 3—complete compression) the important direction is the line of minimum compression.

Figure 2A:
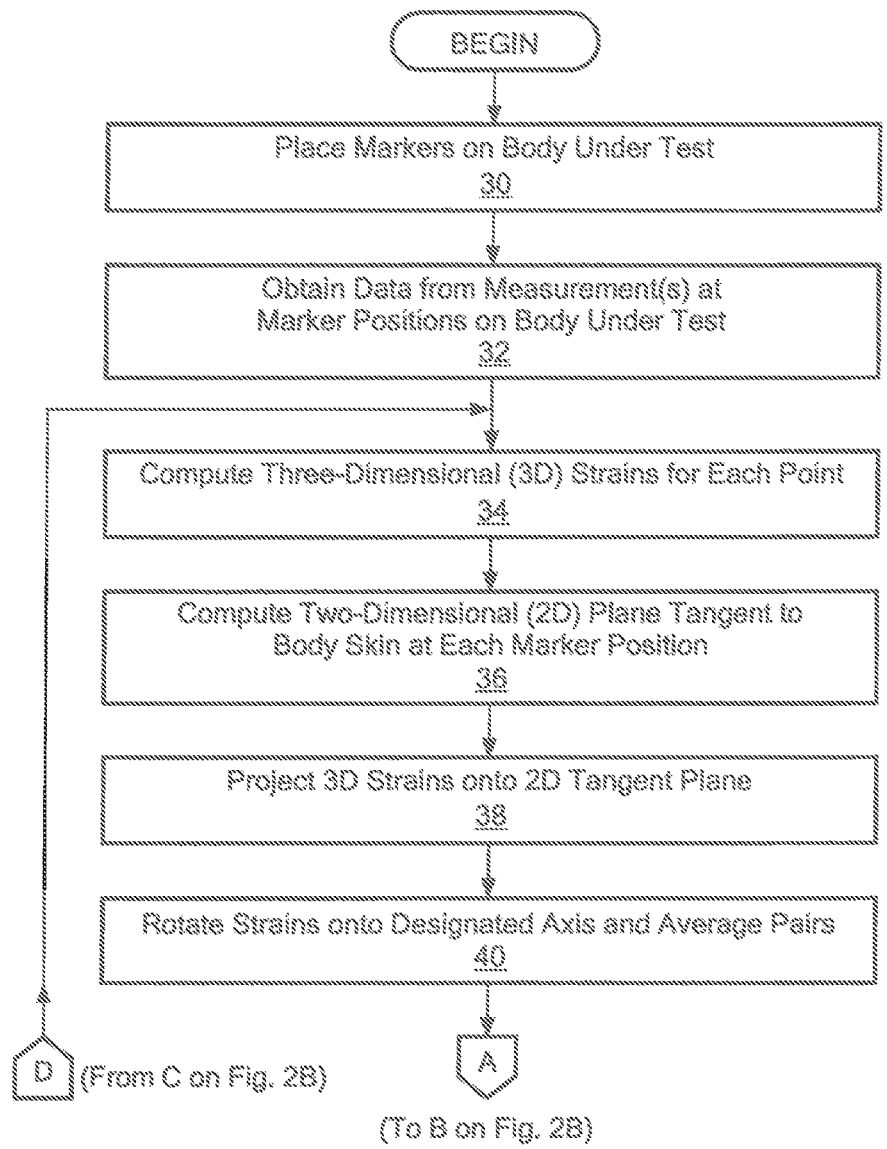
FIGS. 2 and 2B are a series of flow diagrams that illustrate a process for recording body positions and movements; motions for measuring skin strain along a body (a strain field) while a join is in motion (dynamic) as well as in a fixed position (static)
Figure 2B:
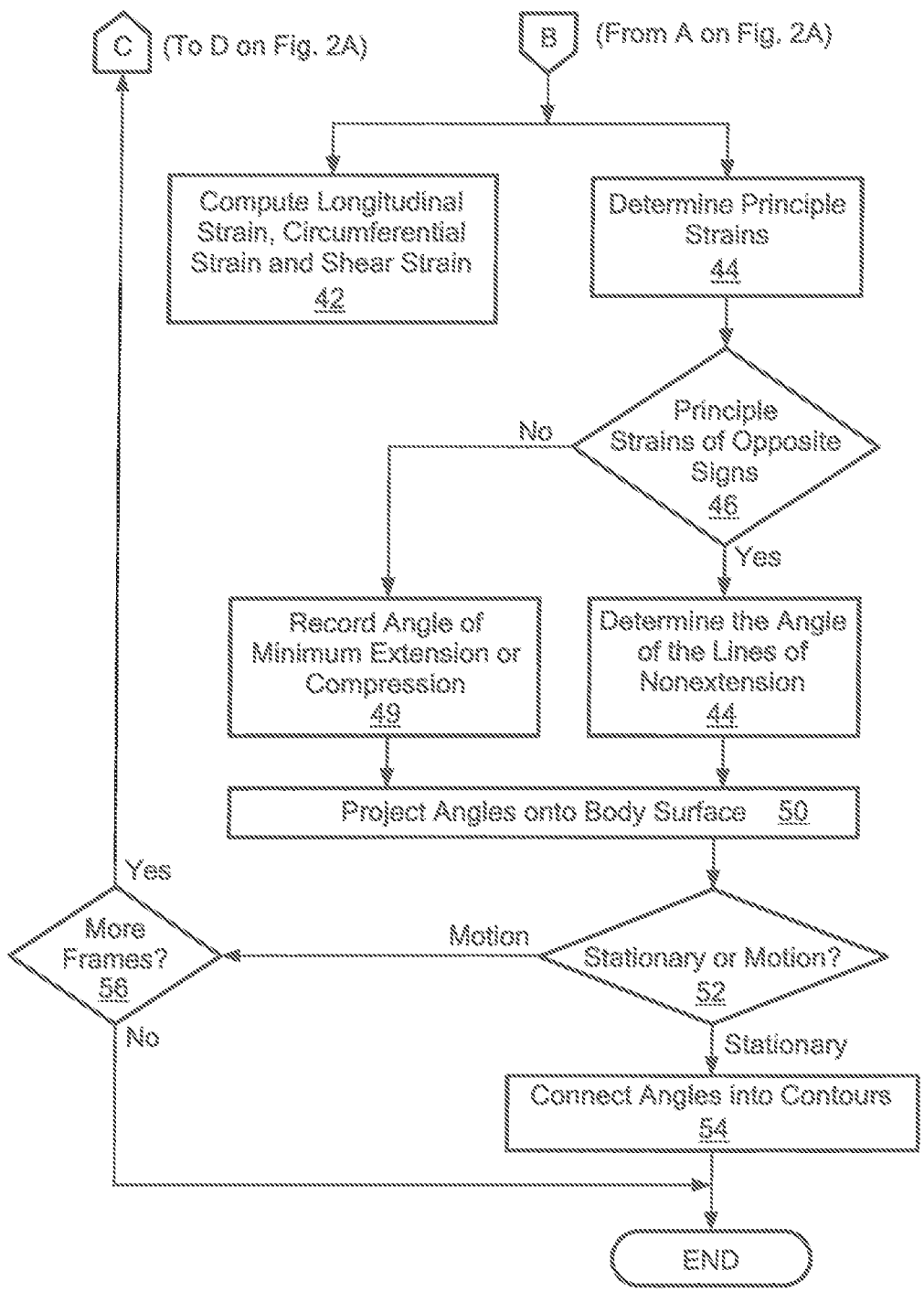

Referring now to FIGS. 2A and 2B, a process for measuring the skin's strain all along the body (a strain field) while a joint is in motion (dynamic) as well as in a fixed position (static) begins by placing markers on a body (or a portion of a body) under test to mark the points at which data will be obtained as shown in block 30. One particular example of marker placement on a knee is described in detail below in conjunction with FIGS. 3A, 3B. It should, of course, be appreciated that the particular placement of markers depends upon a variety of factors including, but not limited to, the portion of the body being measured (e.g. knee, elbow, etc. . . . ), and the limitations of the tracking system.

As shown in block 32, once the markers are placed such that acceptable data can be obtained, a measurement system obtains data at each marker position. In one exemplary embodiment, the measurement system includes a motion capture system (including, for example, a camera, video acquisition, processing and tracking markers) and a three-dimensional (3D) tracking system (e.g. a laser scanner) which record body positions and movements/motions (i.e. measurement are made while the body (or body portion—e.g. joint) is in motion (dynamic) as well as in a fixed position (static). One exemplary system is described below in conjunction with FIG. 6.

Once the data is collected, as shown in block 34, 3D strain values are computed for each point. In one embodiment, second order Lagrangian strains ε are calculated using the following equation:

$$\varepsilon = \frac{l^2 - l_0^2}{2l_0^2} = \frac{\Delta l}{l_0} + \frac{(\Delta l)^2}{2l_0^2};$$

In which:
  l is the new distance between two points
  $l_0$ is the original length between two points, and
  Δl is the difference between the two.

Figure 6:
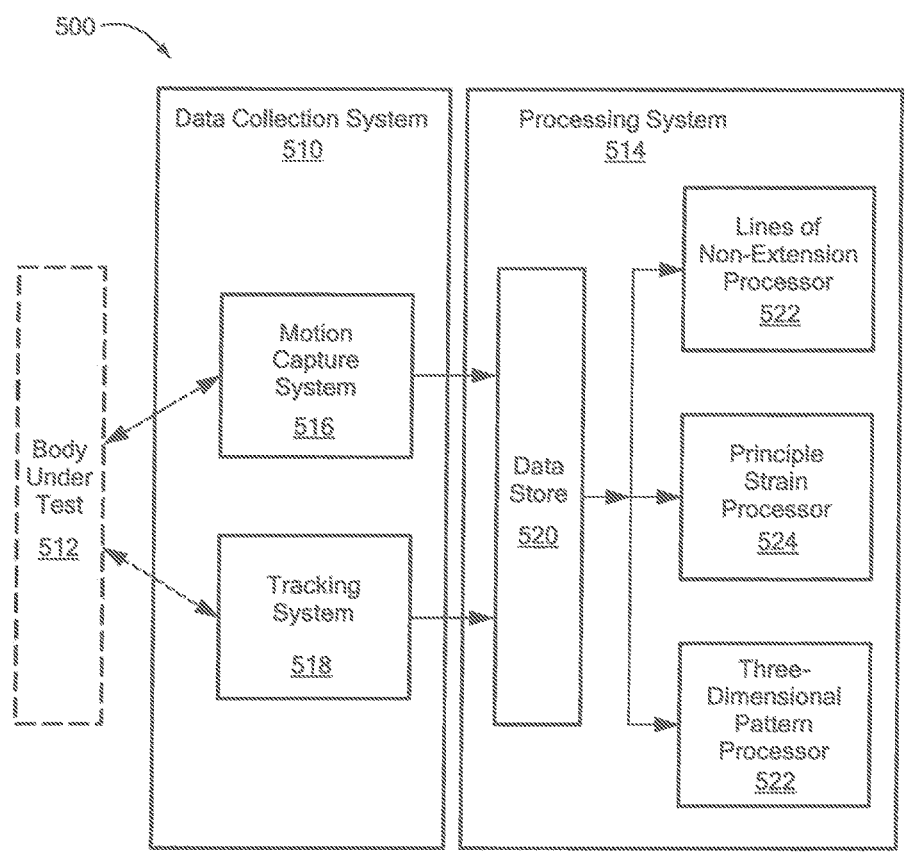
FIG. 6 is a block diagram of a system for measuring and modeling skin movement and for quantifying skin movement and deriving strain fields, contours and three-dimensional patterns.

Processing then proceeds to processing block 36 in which a two-dimensional (2D) plane tangent to the body skin at each marker position is computed. In one embodiment, the two-dimensional (2D) plane is created by first averaging the normal vectors to the planes between each neighboring pair of strain vectors. This new "average" normal of eight (8) different planes defines the normal vector to the tangential plane created at the marker position. It should be appreciated that other techniques may also be used to compute this plane. However, it is believed that this technique yields the most accurate results if a measurement system of the type described below in conjunction with FIG. 6 is used.

Once the two-dimensional (2D) plane tangent to the body skin at each marker position is computed, the 3D strains are projected onto the 2D tangent planes as shown in block 38.

Figure 4B:
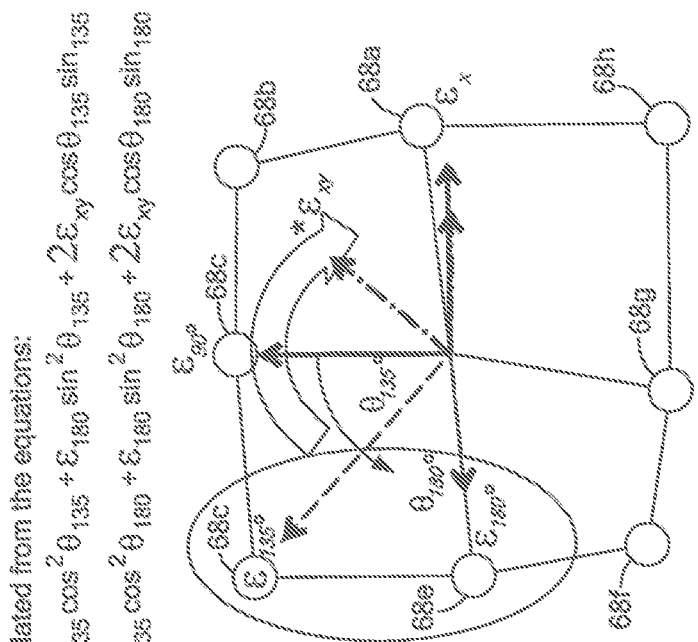
FIGS. 4A and 4B are a graphical explanation of how strain pairs are rotated onto the new axes defined by the position of the marker directly above.
Figure 4A:
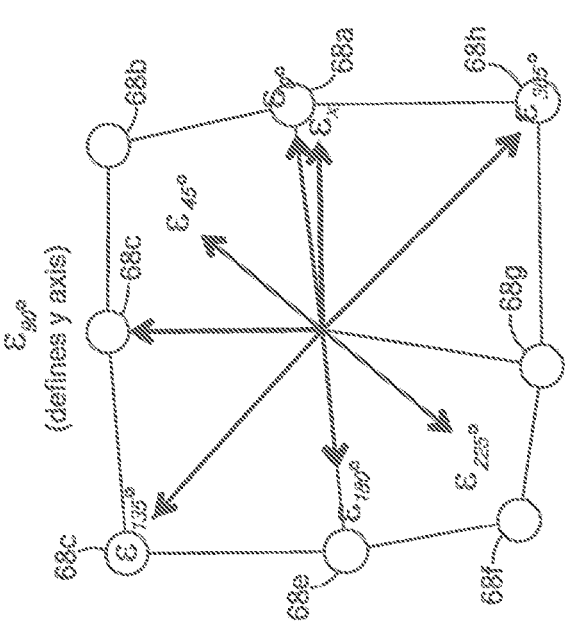

Next, as shown in blocks 40 and 42, longitudinal strain ($\varepsilon_y$), the circumferential strain ($\varepsilon_x$), and the shear strain ($\varepsilon_{xy}$) are computed (see FIGS. 4A, 4B). In one embodiment, this is accomplished in the following manner. After the 3D strains are projected onto the tangential plane (processing block 38), the strains are then rotated in pairs onto the axes defined by the location of the marker directly above (as illustrated in FIGS. 4A and 4B below) and then averaged together to give the longitudinal strain ($\varepsilon_y$), the circumferential strain ($\varepsilon_x$), and the shear strain ($\varepsilon_{xy}$).

Also, as shown in processing block 44, the principle strains ($\varepsilon_I$ and $\varepsilon_{II}$) are determined. In one embodiment, this is accomplished via an eigenvector analysis to determine the principle strains ($\varepsilon_I$ and $\varepsilon_{II}$).

As shown in decision block 46, if the principle strains are of opposite signs, meaning there is both extension and compression, they are used to mathematically determine the angle of the lines of non-extension (φ) as shown in block 48. In one embodiment this can be accomplished with the equations:

$$\tan^2\phi = \frac{\varepsilon_I(2 + \varepsilon_I)}{-\varepsilon_{II}(2 + \varepsilon_{II})}$$

$$\tan^2\phi = \frac{(1 - \varepsilon_I)^2(\varepsilon_I(2 + \varepsilon_I))}{(1 + \varepsilon_{II})^2(1 - (1 + \varepsilon_{II})^2)}$$

where the first equation is the angle between the primary eigenvector and the line of non-extension projected onto the initial position and the second equation is the same angle projected onto the deformed position.

Processing then flows to block 50, in which these angles are projected onto the body surface (e.g., leg).

Processing then flows to decision block 52. If decision block 52 indicates that stationary analysis should be performed (i.e. only a single frame from the imaging system is being processed) then processing proceeds to block 54 and, during stationary analysis, the angles are connected to continuous lines (i.e. contours) using basic spline functions. It should be noted that techniques other than spline functions can also be used to connect to the continuous lines (including but not limited to two straight lines, etc). To date, however, it has been found that a spline is the smoothest and simplest technique. It should also be noted that the above-described method of finding tangent planes and creating strain tensors requires all eight (8) surrounding points. Processing then ends.

If, on the other hand, a decision is made in decision block 46 that the principle strains are of the same sign, meaning there is only local extension or local compression, then the minimum extension or minimum compression is recorded, respectively, as shown in block 49. Processing then flows to decision block 52 and to appropriate ones of blocks 54, 56 as described above. If decision block 52 indicates that motion analysis should be performed (i.e. the imaging system produces multiple frames to capture motion of a body part), then processing flows to decision block 56 which implements a loop in which the process from blocks 34 to 56 is repeated until all frames are processed. Once all frames are processed, then processing ends.

Figure 3A:
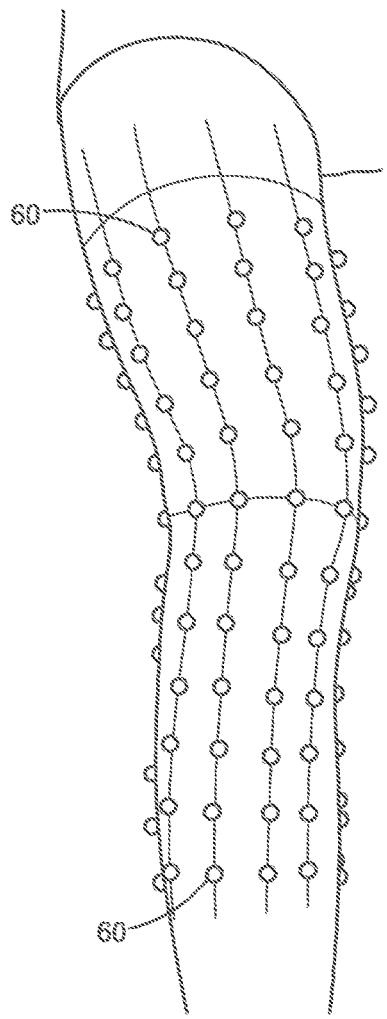
FIGS. 3A and 3B illustrate exemplary placement of one hundred forty four (144) four 4 millimeter (mm) and 6 mm infrared reflecting, spherical markers on a right leg.
Figure 3B:
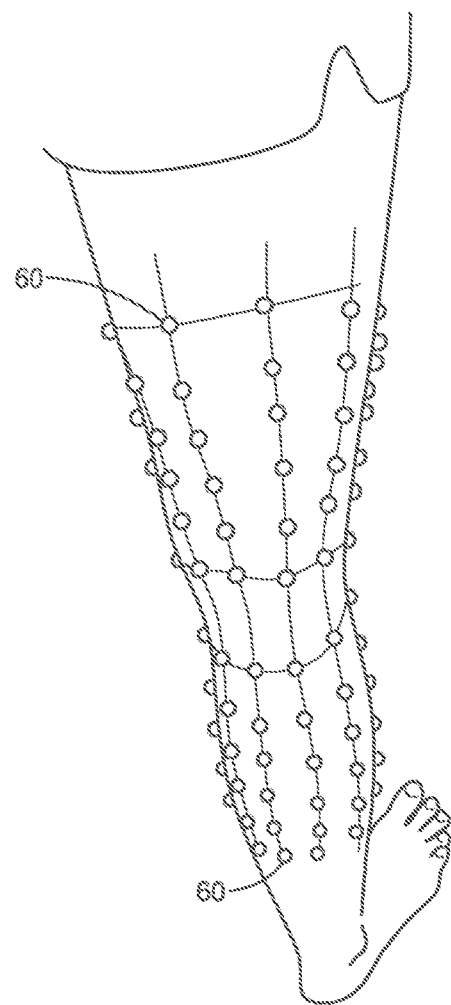

Referring now to FIGS. 3A and 3B, a body part has a plurality of exemplary reflecting, spherical markers, generally denoted 60, disposed thereon. In this exemplary embodiment, the body part is a right leg having one hundred and forty-four (144) markers 50 disposed thereon. It should be noted that FIG. 3A shows the anterior of the leg and FIG. 3B shows the posterior of the right leg.

Also, in this exemplary embodiment, the markers are provided as four millimeter (4 mm) and six (6) mm infrared reflecting, spherical markers. It should, of course, be appreciated that other types, sizes and shapes of markers may be used, In short, any marker which allows the collection of data suitable for use in the processing described herein may be used.

Referring now to FIGS. 4A and 4B, a graphical explanation is shown of how strain pairs are rotated onto the new axes defined by the position of the marker directly above. Eight points 68a-68h are used. It should be noted that the point corresponding to $\varepsilon_{270}$ is not used because its similarity to $\varepsilon_y$ causes large error. The strain values $\varepsilon_{xy}$ and $\varepsilon_x$ are averaged for the final results.

Figure 5C:
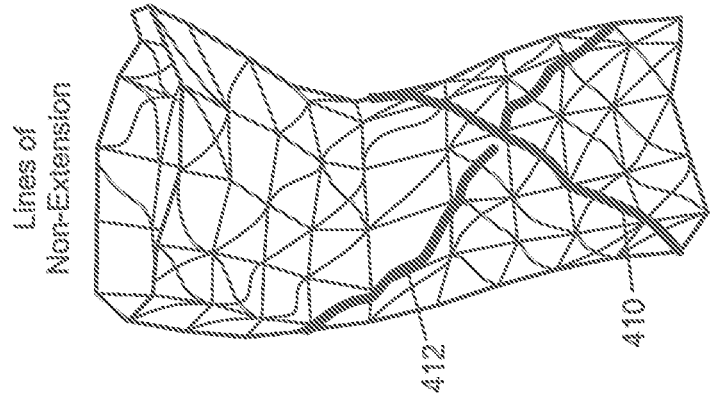
FIG. 5C shows a pattern of lines of non-extension calculated from the strain field seen in FIG. 4B.
Figure 5B:
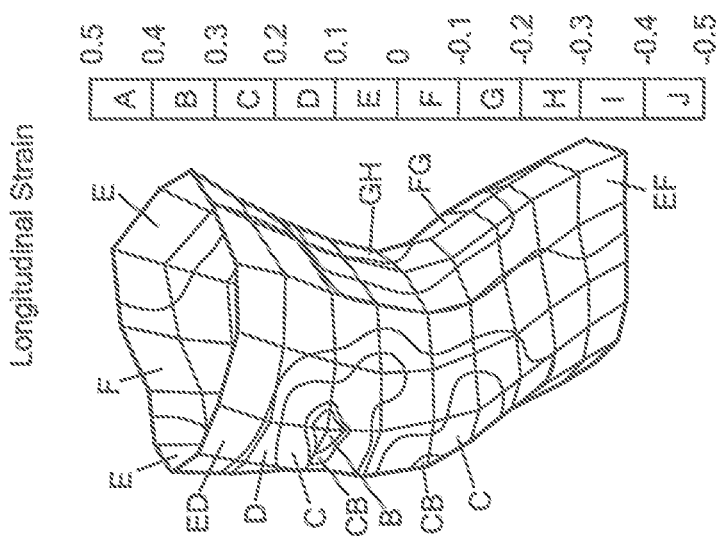
FIG. 5B is a map of longitudinal strains that occur as the leg moves from extended to flexed.
Figure 5A:
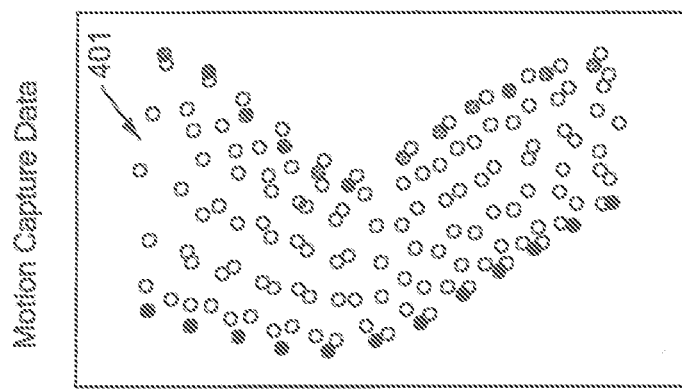
FIG. 5A illustrates a motion capture reconstruction of reflective markers on a bent leg.

FIG. 5A illustrates a motion capture reconstruction of reflective markers on a bent leg. The left-most column 401 indicates the anterior of the leg.

FIG. 5B is a map of longitudinal strains that occur as the leg moves from an extended position to a flexed position.

FIG. 5C shows a pattern of lines of non-extension calculated from the strain field seen in FIG. 5B. Two lines 410, 412 consistent with the pattern on the posterior of the knee are highlighted.

Referring now to FIG. 6 a system 500 for measuring and modeling skin movement and for quantifying skin movement and deriving strain fields, contours and three-dimensional patterns includes a data collection system 510 which collects data from an appropriately marked body under test 512. System 500 is appropriate, for example, to perform the measurement and data processing techniques described herein.

Significantly, data collection system collects from the body under test while the body is at rest (i.e. static data collection) and while the body is undergoing a motion (i.e. dynamic data collection). It should be appreciated that body under test 512 is here shown in phantom since it is not properly a part of the system 500 for measuring and modeling skin movement and for quantifying skin movement and deriving strain fields, contours and three-dimensional patterns.

Data collection system 510 provides the data to a processing system 514 which processes the data to model and quantify skin movement and to derive strain fields, contours and three-dimensional patterns in accordance with the techniques described hereinabove.

In the exemplary embodiment of FIG. 5, data collection system 510 includes a motion capture system 516 and a tracking system 518 which may be provided for example as a three-dimensional laser tracker system. In one embodiment, motion capture system 516 is provided as an eight camera Vicon (Centennial, Colo.) motion capture system.

Motion capture system 510 collects or otherwise obtains position data at the locations of the marker points as discussed above in conjunction with FIGS. 3A, 3B. Data collection system 510 provides the data to processing system 514 and in particular to a data store 520 of processing system 514. Processing system 514 further includes a lines of non-extension (LONEs) processor 522, a principle strain processor 524 and a three-dimensional pattern processor 526 all of which are coupled to receive (either directly or indirectly) data from the data store.

LONEs processor 522 analyzes changes in distance between position data at each marker point and its closest neighbors from initial position to deformation. When a rectangular grid (such as that shown in FIGS. 3A, 3B is used), closest neighbors are considered to be the two markers adjacent in the same row and also the three markers in the rows above and below in the corresponding columns. In one embodiment, because the strains are so large, LONEs processor 522 calculates second order Lagrangian strains using the following equation:

$$\varepsilon = \frac{l^2 - l_0^2}{2l_0^2} = \frac{\Delta l}{l_0} + \frac{(\Delta l)^2}{2l_0^2};$$

In which:
l is the new distance between two points;
$l_0$ is the original length between two points; and
$\Delta l$ is the difference between the two;

LONEs processor 522 then projects the 3D strains surrounding each data point onto a two-dimensional (2D) plane tangent to the body skin at each marker position. The 2D plane is created by first averaging the normal vectors to the planes between each neighboring pair of strain vectors wherein the new average normal of eight (8) different planes defines the normal vector to the tangential plane created at the marker position. After being projected onto the tangential plane the strains are then rotated in pairs onto the axes defined by the location of the marker directly above (as described above in conjunction with FIGS. 4A and 4B) and then averaged together to give the longitudinal strain ($\varepsilon_y$), the circumferential strain ($\varepsilon_x$), and the shear strain ($\varepsilon_{xy}$).

Principle strain processor 524 performs an eigenvector analysis to determine the principle strains ($\varepsilon_I$ and $\varepsilon_{II}$). In response to the principle strains being of opposite signs, meaning there is both extension and compression, they are used to mathematically determine the angle of the lines of non-extension $\phi$ with the known equations:

$$\tan^2\phi = \frac{\varepsilon_I(2 + \varepsilon_I)}{-\varepsilon_{II}(2 + \varepsilon_{II})}$$

$$\tan^2\phi = \frac{(1 - \varepsilon_I)^2(\varepsilon_I(2 + \varepsilon_I))}{(1 + \varepsilon_{II})^2(1 - (1 + \varepsilon_{II})^2)}$$

where the first equation is the angle between the primary eigenvector and the line of non-extension projected onto the initial position and the second equation is the same angle projected onto the deformed position.

In response to the principle strains having the same sign, meaning there is only local extension or local compression, then processor 524 records the minimum extension or minimum compression and projects these angles onto the body surface and, during primarily stationary analysis only, connects them to continuous lines. This may be accomplished, for example, using basic spline functions. This exemplary method of finding tangent planes and creating strain tensors requires all (eight) 8 surrounding points. It should of course be appreciated that in some embodiments less than eight (8) points can be used. In the exemplary embodiment described herein, the eight (8) points (e.g. as illustrated in FIGS. 4A, 4B) are in close proximity and increasing the number of (close) points increases the accuracy of the measurement.

In one embodiment, with respect to stationary data collection, the motion capture system was able to accurately capture a grid of markers spaced approximately 3 cm apart (e.g. as shown in FIG. 5A). Preliminary analysis identified maximum longitudinal strains less than 0.40, within the physical limitations of skin, in an appropriate distribution (FIG. 5B). The process for calculating lines of non-extension from the strain field data (e.g. as described in conjunction with FIGS. 2A, 2B above) found a pattern of lines of non-extension as shown in FIG. 5C.

The entire range of strain (maximum and minimum of the total strain), longitudinal strain, circumferential strain, and sheer strain for each data point are found.

A three-dimensional pattern processor 526 processes the data provided thereto to connect the calculated angles from LONES processor 522 from each data point into anatomically feasible contours. In this way, the system is capable of generating designs for flexible apparel. Such apparel includes but is not limited to athletic or other clothing, portions of space suits and in particular. The system is also useful for generating designs of tissue-engineering scaffolds, medical diagnosis for skin surgery and the design and development of soft exoskeletons.

In one exemplary embodiment the above described technique was utilized on a knee. In this exemplary embodiment, an eight camera Vicon (Centennial, Colo.) motion capture system was used to track one hundred forty four (144) 4-mm and 6-mm spherical reflective markers positioned approximately 3 cm apart around a healthy adult female knee joint with care taken to make a grid with the markers aligned in rows and columns (see FIGS. 3A, 3B). In the exemplary embodiment shown in FIGS. 3A, 3B the markers are disposed in a substantially rectangular grid pattern. Other patterns (both grid and non-grid patterns—e.g. lattice patterns) may, of course, also be used. In preferred embodiments, the markers are disposed in a uniform grid pattern. Such a grid pattern facilitates use of nearest neighbor computations. It should also be appreciated that the distance between markers impacts the accuracy of anatomical representations and the ability to make physiological implications. Thus, the closer the spacing of the markers, the more accurate the anatomical representation and the greater the ability to make physiological implications based upon the anatomical representation. Of course, by spacing markers more closely in a given area (e.g. 1 cm spacing or less), the larger the number of data points which will be generated and consequently the more time it takes to perform computations. Thus, a trade-off may be made between the amount of data needed and the time required to measure and process the data. In one embodiment, the resolution of the motion capture system is the limiting factor in selecting spacing between markers.

With the markers are properly positioned, stationary (i.e. static) data collection is performed. Position data is captured by the motion capture system with the body joint (e.g., knee) extended (initial position) and then again with the body joint flexed (final position).

The acquired position data is filtered and averaged so there is one position for each marker in each position, which then serves as input to the analysis/calculations methodology described above.

Also, with the markers properly positioned, motion (i.e. dynamic) data collection can be performed. It should be noted that the same body marker grid should be used in both the stationary (i.e. static) data collection and the motion (dynamic) data collection. Motion capture position data are collected for an entire flexion and extension cycle (~6 seconds) for the entire movement for every/any body joint. In the dynamic case (e.g. 2-6 seconds of movement captured at a rate of about 15-30 frames per second), an analysis program compares each frame to the initial position (first frame). The resultant output is strain data for each point that can be combined and analyzed over time or for the duration of the movement. Significantly, the system also can be used to produce video files to display the strain and directions of the non-extending lines graphically on a 3D reconstruction of the body (e.g., leg).

The technique described herein allows new data to be generated and with this new data, one can calculate the lines of non-extension, or contours of the skin that remain a constant length during motion as described herein above.

The system and techniques described herein result in a new understanding of the relationship between the structure of skin and the strains it experiences during natural joint movement. The system and techniques described herein may find application in a wide variety of areas including, but not limited to, design of tissue-engineering scaffolds, medical diagnosis for skin surgery, the design and development of soft exoskeletons, commercial spacesuits and athletic garments.

It should also be appreciated that the above-described techniques can be used to calculate the angle of the line of non-extension, line of minimum extension, or line of minimum compression for each frame.

Figure 7:
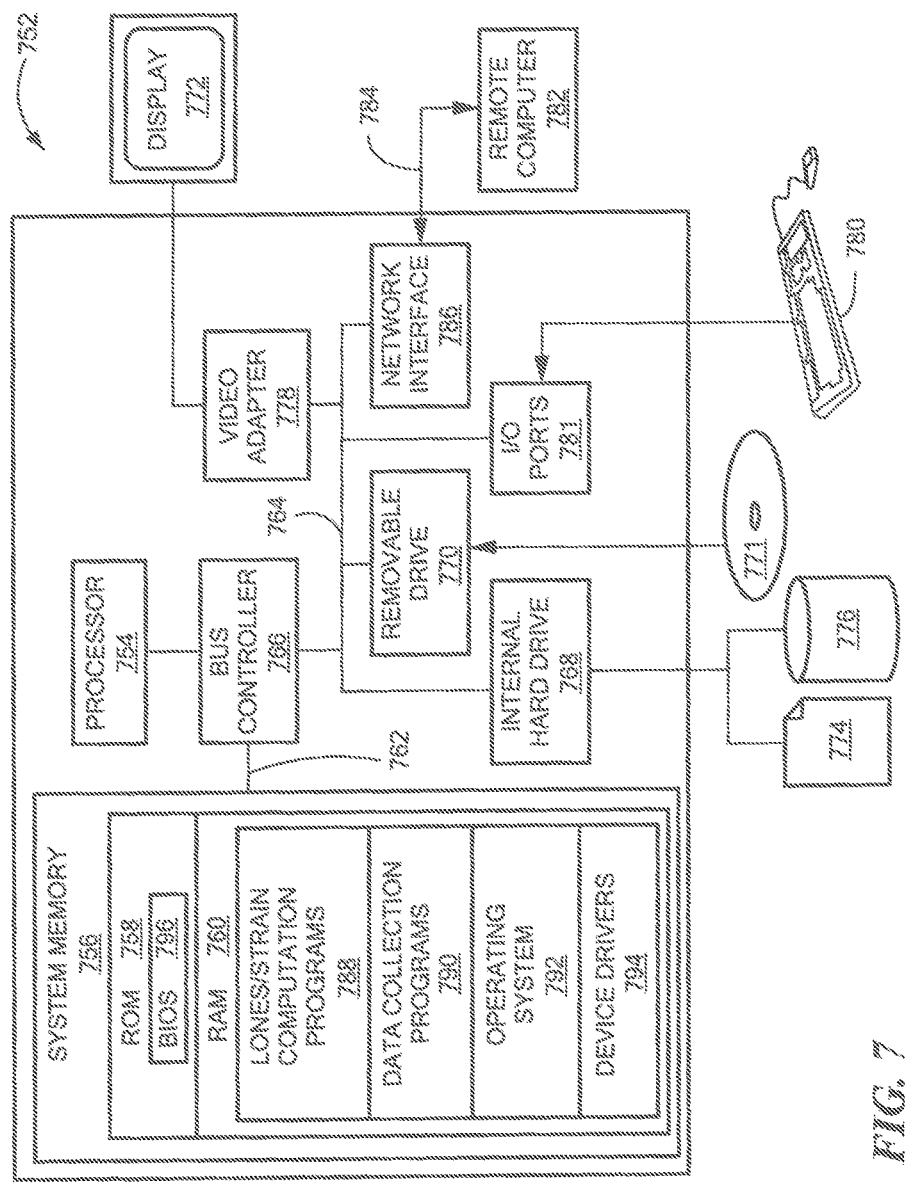
FIG. 7 is a block diagram of a processor of the type which may be used in the system of FIG. 6.

Referring now to FIG. 7, a computer 752 suitable for supporting the operation of an embodiment of the inventive systems, concepts, and techniques described herein includes a processor 754. Processor 754 may, for example, be provided as a dual-core processor, such as one of the types available from the Advanced Micro Devices Corporation of from Intel Corporation. However, it should be understood that computer 752 may use other microprocessors. Computer 752 can represent any server, personal computer, laptop, or even a battery-powered mobile device such as a hand-held personal computer, personal digital assistant, or smart phone.

Computer 752 includes a system memory 756 which is connected to the processor 754 by a system data/address bus 762. System memory 756 includes a read-only memory (ROM) 758 and random access memory (RAM) 760. The ROM 758 represents any device that is primarily read-only including electrically erasable programmable read-only memory (EEPROM), flash memory, etc. RAM 760 represents any random access memory such as Synchronous Dynamic Random Access Memory (SDRAM). The Basic Input/Output System (BIOS) 196 for the computer 752 is stored in ROM 758 and loaded into RAM 760 upon booting.

Within the computer 752, input/output (I/O) bus 764 is connected to the data/address bus 762 via a bus controller 766. In one embodiment, the I/O bus 764 is implemented as a Peripheral Component Interconnect (PCI) bus. The bus controller 766 examines all signals from the processor 754 to route signals to the appropriate bus. Signals between processor 754 and the system memory 756 are passed through the bus controller 766. However, signals from the processor 754 intended for devices other than system memory 756 are routed to the I/O bus 764.

Various devices are connected to the I/O bus 764 including internal hard drive 768 and removable storage drive 770 such as a CD-ROM drive used to read a compact disk 771 or a floppy drive used to read a floppy disk. The internal hard drive 768 is used to store data, such as in files 774 and database 776. Database 776 may include, for example, a structured collection of data, such as a relational database. A display 772, such as a cathode ray tube (CRT), liquid-crystal display (LCD), etc. is connected to the I/O bus 764 via a video adapter 778.

A user enters commands and information into the computer 752 by using input devices 780, such as a keyboard and a mouse, which are connected to I/O bus 764 via I/O ports 781. Other types of pointing devices that may be used include track balls, joy sticks, and tracking devices suitable for positioning a cursor on a display screen of the display 772.

Computer 752 may include a network interface 786 to connect to a remote computer 782, an intranet, or the Internet via network 784. The network 784 may be a local area network or any other suitable communications network. Data from external systems (e.g. a data collection system such as that described above in conjunction with FIG. 6) may be provided tom computer 752 through various computer I/O ports and/or network connections.

Computer-readable modules and applications 788 and other data are typically stored on memory storage devices, which may include the internal hard drive 768 or the compact disk 771, and are copied to the RAM 760 from the memory storage devices. In one embodiment, computer-readable modules and applications 788 are stored in ROM 758 and copied to RAM 760 for execution, or are directly executed from ROM 758. In still another embodiment, the computer-readable modules and applications 788 are stored on external storage devices, for example, a hard drive of an external server computer, and delivered electronically from the external storage devices via network 784.

The computer-readable modules 788 may include compiled (or compilable) instructions for implementing embodiments of one or more of: a LONEs processor, a principle strains processor or a skin orientation processor and methods described herein. Skin movement and/or strain data may be rendered and outputted to display 772 to enable users to graphically view the data (e.g. as shown in FIGS. 3A-5C).

In a further embodiment, the computer 752 may execute various processes on separate processors, such as a first processor and a second processor of a dual core processor. As by way of a non-limiting example, control of data collections operations (e.g. to receive and respond to data from a data collection system) may be executed by the first processor and skin and strain operations (e.g., to compute LONEs and strain values) may be executed by the second processor. Alternatively, the first and second processors may be respective first and second computing devices.

The computer 752 may execute a database application 790, such as Oracle™ database from Oracle Corporation, to model, organize, and query data stored in database 776. The data may be used by the computer-readable modules and applications 788 and/or passed over the network 784 to the remote computer 782 and other systems.

In general, the operating system 792 executes computer-readable modules and applications 788 and carries out instructions issued by the user. For example, when the user wants to execute a computer-readable module 788, the operating system 792 interprets the instruction and causes the processor 754 to load the computer-readable module 788 into RAM 760 from memory storage devices. Once the computer-readable module 788 is loaded into RAM 760, the processor 754 can use the computer-readable module 788 to carry out various instructions. The processor 754 may also load portions of computer-readable modules and applications 788 into RAM 760 as needed. The operating system 792 uses device drivers 794 to interface with various devices, including memory storage devices, such as hard drive 768 and removable storage drive 770, network interface 786, I/O ports 781, video adapter 778, and printers.

It should be appreciated that the processes described herein (e.g. in conjunction with FIGS. 2A and 2B, for example) are not limited to use with the hardware and software of FIG. 7. Rather, they may find applicability in any computing or processing environment and with any type of machine or set of machines that is capable of running a computer program.

It should also be appreciated that the processes described herein (e.g. in conjunction with FIGS. 2A and 2B, for example) may be implemented in hardware, software, or a combination of the two. The processes described herein may be implemented in computer programs executed on programmable computers/machines that each includes a processor, a storage medium or other article of manufacture that is readable by the processor (including volatile and nonvolatile memory and/or storage elements), at least one input device, and one or more output devices. Program code may be applied to data entered using an input device to perform one or more of the processes and/or to generate output information.

The system may be implemented, at least in part, via a computer program product, (e.g., in a machine-readable storage device), for execution by, or to control the operation of, data processing apparatus (e.g., a programmable processor, a computer, or multiple computers)). Each such program may be implemented in a high level procedural or object-oriented programming language to communicate with a computer system. However, the programs may be implemented in assembly or machine language. The language may be a compiled or an interpreted language and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network. A computer program may be stored on a storage medium or device (e.g., CD-ROM, hard disk, or magnetic diskette) that is readable by a general or special purpose programmable computer for configuring and operating the computer when the storage medium or device is read by the computer to perform processes. The processes described herein may also be implemented as a machine-readable storage medium, configured with a computer program, where upon execution, instructions in the computer program cause the computer to operate in accordance with processes.

The processes described herein are not limited to the specific embodiments described. For example, the process described in FIGS. 2A and 2B are not limited to the specific processing order shown in FIGS. 2A and 2B, respectively. Rather, unless otherwise precluded, any of the processing blocks of FIGS. 2A and 2B may be re-ordered, combined or removed, performed in parallel or in serial, as necessary, to achieve the results set forth above.

The processing described herein (e.g. in conjunction with FIGS. 2A, 2B) associated with implementing the system and/or the techniques described herein may be performed by one or more programmable processors executing one or more computer programs to perform the functions of the system. All or part of the system may be implemented as, special purpose logic circuitry (e.g., an FPGA (field programmable gate array) and/or an ASIC (application-specific integrated circuit)) and/or neural networks.

Also, it should be appreciated that elements of different embodiments described herein may be combined to form other embodiments not specifically set forth above. Other embodiments not specifically described herein are also within the scope of the following claims.

Having described preferred embodiments of the concepts, systems, circuits and techniques described herein, it will now become apparent to those of ordinary skill in the art that other embodiments incorporating these concepts may be used. For example, it should now be appreciated that one can apply the topologies described herein to rectifier systems (e.g. for grid-connected power supplies) as well and for bidirectional power flow converter systems. Accordingly, it is submitted that that the concepts, systems, circuits and techniques described herein, should not be limited to the described embodiments but rather should be limited only by the spirit and scope of the appended claims.

The invention claimed is:

1. A method for computing lines of non-extension (LONEs) in a skin movement and strain measurement system, the method comprising:
   (a) obtaining, by a motion capture system of the skin movement and strain measurement system, position data by:
       obtaining three-dimensional (3D) positions of a plurality of marker points disposed on body skin surrounding a joint of a test subject with the joint of the test subject in an initial position;
       moving the joint of the test subject to a deformed position; and
       obtaining 3D positions of the marker points with the joint of the test subject in the deformed position, wherein the plurality of marker points form a grid on the body skin of the test subject;
   by a LONEs processor of the skin movement and strain measurement system:
   (b) analyzing changes in distance between each marker point and one or more adjacent marker points from the initial position to the deformed position;
   (c) determining one or more 3D strains surrounding each marker point;
   (d) projecting 3D strains surrounding each marker point onto a two-dimensional (2D) plane tangent to the body skin at the corresponding marker point;
   (e) after projecting 3D strains onto the 2D tangential plane for each marker point, rotating the projected strains in pairs onto axes defined with respect to the location of the corresponding marker point;
   (f) averaging the rotated pairs for each axis associated with each marker point to generate a longitudinal strain ($\varepsilon_y$), a circumferential strain ($\varepsilon_x$), and a shear strain ($\varepsilon_{xy}$);
   (g) determining principle strains ($\varepsilon_I$ and $\varepsilon_{II}$) for each marker point;
   (h) if the principle strains associated with a first marker point have opposite signs, determining an angle of a line of non-extension for the first marker point using the principle strains associated with the first marker point; and
   (i) if the principle strains associated with the first marker point have the same sign, recording an angle of minimum extension or minimum compression for the first marker point and projecting the angle of minimum extension or minimum compression onto the body surface.

2. The method of claim 1 further comprising:
   repeating (h) and (i) for other marker points in the plurality of marker points; and
   connecting angles of lines of non-extension into contours.

3. The method of claim 1 wherein:
   obtaining 3D positions of the marker points comprises obtaining 3D positions of the marker points with the joint of the test subject in positions other than the initial position and the deformed position as part of a motion analysis; and
   repeating (b) through (i) for successive frames of the motion analysis.

4. The method of claim 1 wherein determining one or more 3D strains surrounding each marker point comprises calculating second order Lagrangian strains using the following equation:

$$\varepsilon = \frac{l^2 - l_0^2}{2l_0^2} = \frac{\Delta l}{l_0} + \frac{(\Delta l)^2}{2l_0^2};$$

in which:
$\varepsilon$ is the second order Lagrangian strain for two points;
l is a new distance between the two points;
$l_o$ is an original distance between the two points; and
$\Delta l$ is a difference between the new distance and the original distance.

5. The method of claim 1 wherein determining an angle of a line of non-extension for the first marker point using the principle strains associated with the first marker point includes using the equations:

$$\tan^2\phi = \frac{\varepsilon_I(2+\varepsilon_I)}{-\varepsilon_{II}(2+\varepsilon_{II})}$$

$$\tan^2\phi = \frac{(1-\varepsilon_I)^2(\varepsilon_I(2+\varepsilon_I))}{(1+\varepsilon_{II})^2(1-(1+\varepsilon_{II})^2)}$$

wherein the equations correspond to the angle between a primary eigenvector and the line of non-extension projected onto the initial position and the deformed position, respectively, wherein $\varepsilon_I$ and $\varepsilon_{II}$ are the principle strains.

6. The method of claim 1 further comprising:
   generating the 2D tangential plane for each marker point, before projecting the 3D strains, by averaging normal vectors to the planes between each neighboring pair of strain vectors associated with the corresponding marker point, wherein a neighboring pair of strain vectors comprises strain vectors associated with two closest neighbor marker points that are adjacent to one another.

7. The method of claim 6 wherein averaging normal vectors includes averaging normal vectors associated with eight (8) different planes.

8. The method of claim 1 wherein determining the principle strains ($\varepsilon_I$ and $\varepsilon_{II}$) comprises performing an eigenvector analysis to determine the principle strains ($\varepsilon_I$ and $\varepsilon_{II}$).

9. A method to measure skin movement and strain in a skin movement and strain measurement system, the method comprising:
   (a) obtaining position data associated with body skin of a test subject using a motion capture system of the skin movement and strain measurement system, the position data corresponding to a plurality of marker points disposed on the body skin around a joint of the test subject, wherein obtaining position data includes obtaining position data for multiple different orientations of the joint of the test subject;
   (b) computing, by a processor of the skin movement and strain measurement system, angles of lines of nonextension (LONEs) for various marker points on the body skin of the test subject using the collected position data by:
  determining one or more three-dimensional (3D) strains surrounding each marker point;
  computing a two-dimensional (2D) plane tangent to the body skin at each marker point at which position data of body skin was taken in (a);
  projecting the 3D strains surrounding each marker point onto the corresponding 2D plane tangent to the body skin;
  computing values for longitudinal strain ($\varepsilon_y$), circumferential strain ($\varepsilon_x$), and shear strain ($\varepsilon_{xy}$) for each marker point;
  determining principle strains ($\varepsilon_I$ and $\varepsilon_{II}$) for each marker point;
  if the principle strains associated with a first marker point have opposite signs, using the principle strains to mathematically determine an angle of a line of non-extension for the first marker point; and
(c) connecting the angles of lines of non-extension into contours for use in performing at least one of: flexible apparel design, tissue-engineering scaffold design, soft exoskeleton design, and skin surgery.

10. The method of claim 9 wherein computing angles of lines of non-extension further comprises:
  repeating (b) for other marker points within the plurality of marker points.

11. The method of claim 10 further comprising if the principle strains associated with the first marker point have a common sign, recording an angle of minimum compression or minimum extension for the first marker point.

12. The method of claim 10 further comprising projecting strains onto the surface for analysis.

13. The method of claim 9, wherein determining one or more 3D strains surrounding each marker point comprises calculating second order Lagrangian strains using the following equation:

$$\varepsilon = \frac{l^2 - l_0^2}{2l_0^2} = \frac{\Delta l}{l_0} + \frac{(\Delta l)^2}{2l_0^2};$$

in which:
  $\varepsilon$ is the second order Lagrangian strain for two points;
  l is a new distance between the two points;
  $l_o$ is an original distance between the two points; and
  $\Delta l$ is a difference between the new distance and the original distance.

14. A method to measure skin movement and strain in a skin movement and strain measurement system, the method comprising:
  (a) obtaining position data of body skin using a motion capture system of the skin movement and strain measurement system, wherein obtaining position data comprises obtaining three dimensional (3D) positions of a plurality of marker points disposed on the body skin surrounding a joint of a test subject with the joint of the test subject in an initial position, moving the joint of the test subject to a deformed position, and obtaining 3D positions of the marker points with the joint of the test subject in the deformed position, wherein the plurality of marker points form a grid on the body skin of the test subject;
  (b) analyzing, by a processor of the skin movement and strain measurement system, changes in distance between each marker point and one or more adjacent marker points from the initial position to the deformed position;
  (c) determining one or more 3D strains surrounding each marker point;
  (d) generating a two-dimensional (2D) plane tangent to the body skin at each marker point by averaging normal vectors to the planes between each neighboring pair of strain vectors associated with the corresponding marker point, wherein a neighboring pair of strain vectors comprises strain vectors associated with two closest neighbor marker points that are adjacent to one another;
  (e) projecting the 3D strains surrounding each marker point onto the corresponding 2D plane;
  (f) after projecting the 3D strains onto the 2D tangential plane for each marker point, rotating the projected strains in pairs onto axes defined with respect to the corresponding marker point;
  (g) averaging the rotated pairs for each axis associated with each marker point to generate a longitudinal strain value ($\varepsilon_y$), a circumferential strain value ($\varepsilon_x$), and a shear strain value ($\varepsilon_{xy}$) for the marker point;
  (h) determining principle strain values ($\varepsilon_I$ and $\varepsilon_{II}$) for each marker point using eigenvector analysis;
  (i) if the principle strain values associated with a marker point have opposite signs, using the principle strain values to determine an angle of a line of non-extension for the marker point; and
  (j) if the principle strain values associated with a marker point have a common sign, recording an angle of minimum extension or an angle of minimum compression for the marker point.

15. The method of claim 14 wherein obtaining position data comprises obtaining 3D positions of the marker points with the joint of the test subject in positions other than the initial position and the deformed position.

16. The method of claim 14 wherein determining one or more 3D strains surrounding each marker point comprises computing one or more second order Lagrangian strains.

17. The method of claim 14 wherein generating a 2D plane tangent to the body skin at each marker point includes averaging eight normal vectors for each marker point.

18. The method of claim 14 wherein using the principle strains associated with a marker point to determine the angle of a line of non-extension for the marker point comprises using the principle strains to mathematically determine the angle of the line of non-extension using the equations:

$$\tan^2\phi = \frac{\varepsilon_I(2+\varepsilon_I)}{-\varepsilon_{II}(2+\varepsilon_{II})}$$

$$\tan^2\phi = \frac{(1-\varepsilon_I)^2(\varepsilon_I(2+\varepsilon_I))}{(1+\varepsilon_{II})^2(1-(1+\varepsilon_{II})^2)}$$

wherein the equations correspond to the angle between a primary eigenvector and the line of non-extension projected onto the initial position and the deformed position, respectively, wherein $\varepsilon_I$ and $\varepsilon_{II}$ are the principle strains.

19. The method of claim 14 further comprising projecting the angle of minimum extension or the angle of minimum compression for the marker point onto the body skin.

20. The method of claim 16, wherein calculating second order Lagrangian strains comprises using the following equation:

$$\varepsilon = \frac{l^2 - l_0^2}{2l_0^2} = \frac{\Delta l}{l_0} + \frac{(\Delta l)^2}{2l_0^2};$$

in which:
- $\varepsilon$ is the second order Lagrangian strain for two points;
- $l$ is a new distance between the two points;
- $l_o$ is an original distance between the two points; and
- $\Delta l$ is a difference between the new distance and the original distance.

* * * * *